United States Patent [19]

Grill et al.

[11] 4,144,351
[45] Mar. 13, 1979

[54] SUBSTITUTED PROPANOL-(2) DERIVATIVES AND THEIR PREPARATION AND USE AS HYPOLIPEMIC DRUGS

[75] Inventors: Helmut Grill, Vaterstetten; Rainer H. Zschocke, Munich; Josef Wagner, Grünwald; Gernot Hofrichter, Vaterstetten, all of Fed. Rep. of Germany; P. Stefan Janiak, Basel, Switzerland

[73] Assignee: Klinge Pharma GmbH & Co., Munich, Fed. Rep. of Germany

[21] Appl. No.: 849,765

[22] Filed: Nov. 9, 1977

Related U.S. Application Data

[62] Division of Ser. No. 641,982, Dec. 18, 1975, Pat. No. 4,073,935.

[30] Foreign Application Priority Data

Dec. 20, 1974 [DE] Fed. Rep. of Germany ....... 2460689

[51] Int. Cl.$^2$ ........................................ A61K 31/335
[52] U.S. Cl. .................................. 424/278; 424/341; 260/340.9 R; 568/644; 568/645
[58] Field of Search ................. 260/340.9 R; 424/278

[56] References Cited

U.S. PATENT DOCUMENTS 2,738,351   3/1956   Dickinson et al. ................ 260/293.4

FOREIGN PATENT DOCUMENTS 730789   2/1943   Fed. Rep. of Germany.
2120396  11/1972  Fed. Rep. of Germany.
2207254   8/1973  Fed. Rep. of Germany.
9000247   5/1974  Japan.

OTHER PUBLICATIONS

Journ. Medicinal Chem., vol. 15, No. 3, pp. 286–291.

*Primary Examiner*—Ethel G. Love
*Attorney, Agent, or Firm*—Brumbaugh, Graves, Donohue and Raymond

[57] ABSTRACT

New 1,3-disubstituted propanol-(2) derivatives and their nicotinic acid esters of the general formula

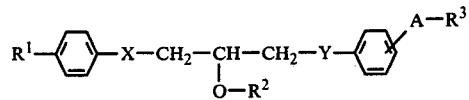

and their therapeutically acceptable salts, processes for preparing the same and the use thereof and pharmaceutical preparations containing the same for the treatment of hyperlipemia.

7 Claims, No Drawings

SUBSTITUTED PROPANOL-(2) DERIVATIVES AND THEIR PREPARATION AND USE AS HYPOLIPEMIC DRUGS

This is a division of application Ser. No. 641,982 filed Dec. 18, 1975, now U.S. Pat. No. 4,073,935.

It is already known that substituted diethers of glycerine, in particular the glycerine ethers of phenol, exhibit therapeutic effects. Thus German Pat. No. 730,789 describes 1-oxyaryloxy-3-alkoxypropanol-(2)s as sedatives and hypnotics, while U.S. Pat. No. 2,738,351 discloses 1,3-bisphenoxypropanol-(2)s. From German Letters of Disclosure No. 2,120,396, it is known further that 1-phenoxy-3-alkoxypropanol-(2)s possess choleretic properties, whose activities may be varied by substitution on the phenyloxy radical, as is shown in German Letters of Disclosure No. 2,207,254. From J. Med. Chem. 1972, p. 286, it is known that 1-phenoxy-3-arylpiperazinyl-propanol-(2) derivatives act on the central nervous system, and Japanese Pat. No. 9,000,247 describes 1-oxycinnamic acid ether derivatives of 3-alkylamino-propanol-(2) as compounds having beta-adrenergic activity with nerve blocking properties.

Surprisingly, it has now been found that certain 1,3-disubstituted propanol-(2) derivatives and their nicotinic acid esters have potent hypolipemic properties.

It is today sufficiently established that elevated serum lipids (hypercholesterolemia and/or hypertriglyceridemia), as so-called "primary risk factors," accelerate development of atherosclerosis. Atheroselerosis, in particular atherosclerotically conditioned coronary heart diseases, have today become the most frequent cause of death in the highly industrialized countries of the West.

This realization carries its prophylactic and therapeutic implications. The recognized risk factor of hyperlipemia must be eliminated to achieve an improvement of the prognosis. Especially 2-(4'-chlorophenoxy)-2-methylpropionic acid ethyl ester (Clofibrate) has been introduced in the treatment of hyperlipemias. It has been found, however, that in many cases Clofibrate fails to give satisfactory therapeutic results.

The object of the present invention was to provide new therapeutically valuable compounds that, with excellent tolerance, would effectively lower in particular the triglyceride level and/or the cholesterol level of the blood.

The invention relates to isopropanol derivatives of general formula

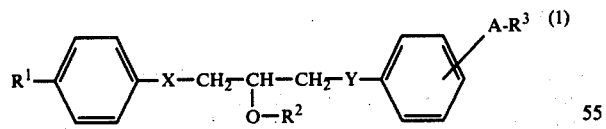

(1)

and their therapeutically acceptable salts, where the X and Y links stand for —O—, or one of them represents —NH—, and X may alternatively be —S— if Y is —O—;

$R^1$ = —Cl, or —C(CH$_3$)$_3$;

$R^2$ = —H,

= nicotinoyl, if X and Y stand for —O—, and X may alternatively be —S—;

A = a valence bond, vinylene or ethylene group;

$R^3$ = —COOH,

= —COOMe, where Me may be sodium, potassium, magnesium as well as aluminum, or represents a therapeutically acceptable ammonium group, = —COOR', where R' is a straight or branched, saturated or unsaturated alkyl radical having 1 to 3 carbon atoms, optionally bearing a terminal hydroxy or methoxy group, a chlorine atom or a dimethylamino group, or the piperidyl-(1) radical, or R' represents a pyridyl-(3)-methyl radical, = —CONHOH if X and Y stand for —O— and X may alternatively be —S—,

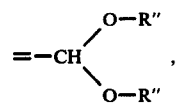

where R" is a methyl or ethyl group if A represents a valence bond, X and Y stand for —O—, and X may alternatively be —S—;

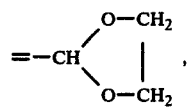

if A represents a valence bond, X and Y stand for —O—, and X may alternatively be —S—.

The manner in which the position of the —A—R$^3$ radical is indicated in formula (1) is intended to show that this radical is in position 3 or 4 relative to the Y link.

The invention relates further to a process for preparing new 1,3-disubstituted propanol-(2) derivatives of general formula (1), characterized in that first, if the Y link is an oxygen atom and R$^3$ represents an alkoxycarbonyl radical, a compound of general formula

(2)

in which R$^1$ stands for a chlorine atom or a tertiary butyl group and -XH for a hydroxyl, amino or mercapto group is reacted with a glycide ether of the general formula

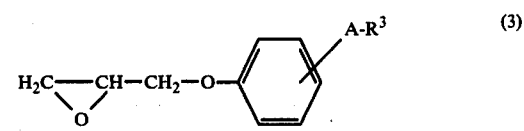

(3)

in which A, in position 3 or 4 in relation to the oxygen atom, stands for a valence bond or a vinylene or ethylene group, and R$^3$ is an alkoxycarbonyl function of the general formula —COOR' where R' is a straight or branched, saturated or unsaturated alkyl radical having 1 to 3 carbon atoms, in protic organic solvents, preferably alcohols, whose alkyl radical is identical with R', in the presence of bases, advantageously alkali metal hydroxides or Lewis acids, for example boron trifluoride ethyl etherate; or, if the X link is an oxygen or sulfur atom and R$^3$ has the meaning given for formula (3), a compound of general formula

 (4)

in which HY— represents a hydroxyl or amino group and the radical —A—R³ in position 3 or 4 has the meaning given for formula (3) is reacted as described above with a glycide ether of the general formula

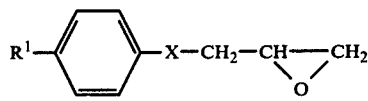 (5)

in which R¹ represents a chlorine atom or a tertiary butyl group and the X link stands for an oxygen or sulfur atoms, and the reaction product is further processed as follows to prepare other carbonyl derivatives.

To prepare the acids according to formula (1), the esters, preferably methyl esters, according to formula (1) are advantageously saponified with aqueous-alcoholic caustic alkali. From the alkali metal salts present in alkaline solution, the acids according to formula (1) may be set free by addition of mineral acids, as for example hydrochloric or sulfuric acid.

Preparation of the salts according to formula (1) is accomplished by allowing the corresonding acids, preferably in aqueous-alcoholic medium, to react with bases of the alkali or alkaline earth series, aluminum bases, as well as ammonia or other therapeutically acceptable amines, by known methods.

Esters according to formula (1), where their preparation is not accomplished on the principle described above, are obtained according to standard methods by esterifying the carboxylic acids according to formula (1) with the corresponding alcohol using an acid catalyst, or by transesterification, preferably the methyl esters according to formula (1) being made to react with another alcohol in the presence of an acid or alkaline catalyst.

Esters according to formula (1) in which the X and Y links stand for —O—, and X may alternatively be —S—, that are obtained neither by esterifying the carboxylic acids nor by transesterifying the methyl esters according to formula (1) are preferably prepared by converting the carboxylic acids according the formula (1), provided with a protective group, advantageously an acetyl or benzyl group, at the secondary hydroxyl, using conventional halogenating agents, preferably thionyl halides, into the reactive acid halides according to formula (1) in which R³ signifies —CO—halogen, reacting the latter in manner known per se with the corresponding alcohols, and then selectively splitting off the protective group by hydrolysis or hydrogenolysis, depending on its nature, without at the same time causing any other irreversible changes in the molecule.

Compounds according to formula (1) in which the X and Y links stand for —O— and A in position 3 or 4 represents an ethylene group and R³ is a carboxyl group or an alkoxycarbonyl group of general formula —COOR' where R' is a straight or branched, saturated alkyl radical having 1 to 3 carbon atoms, may most readily be prepared by subjecting the conveniently accessible compounds according to formula (1) in which A in position 3 or 4 is a vinylene group and R³ has the meaning given above to a catalytic hydrogenation, preferably using Raney nickel as catalyst.

Compounds according to formula (1) in which the X and Y links represent an oxygen atom and X may alternatively be —S—, A in position 3 or 4 stands for a valence bond, a vinylene or an ethylene group, and the radical R³ has the —CONHOH function, may be prepared from the esters according to formula (1), preferably the methyl esters, by reaction with hydroxylamine in protic medium.

Compounds according to formula (1) in which A represents a valence bond and R³ signifies an acetal radical may be prepared by reacting compounds of general formula

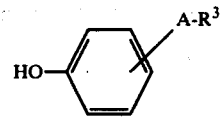 (6)

in which A in position 3 or 4 stands for a valence bond and R³ is a dimethoxymethyl, diethoxymethyl or 1,3-dioxolan-(2)-yl radical with the glycide ethers according to formula (5), where advantageously the phenols according to formula (6) are generated during the reaction itself from the corresponding acetals.

Compounds according to formula (1) in which the radical R² represents a nicotinoyl group are obtained by reacting propanol-(2) derivatives according to formula (1) in which the X and Y links stand for —O— and X may alternatively be —S— with nicotinic acid halides in a manner known per se. Propanol-(2) derivatives according to formula (1) in which R³ signifies —COOH are made to react, for example in the form of their benzyl esters, with nicotinic acid halides, the protective group may then be removed by selective cleavage by hydrogenolysis in the presence of palladium charcoal.

Glycide ethers of general formula (3) may be obtained by reaction of compounds of the general formula

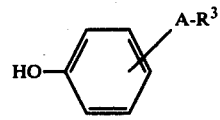 (7)

in which A in position 3 or 4 is a vinylene or ethylene group or a valence bond and R³ stands for an alkoxycarbonyl function of the general formula —COOR' where R' is a straight or branched, saturated or unsaturated alkyl radical having 1 to 3 carbon atoms with epihalogen hydrins, preferably epichlorohydrin, in the presence of bases, preferably alkali metal hydroxides, isolation of the halogen hydrins of the general formula

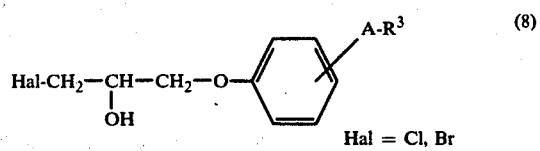 (8)

Hal = Cl, Br primarily formed, where A and R³ have the meaning given above, being optional.

Glycide ethers of the general formula (5) are formed in the reaction of compounds of the general formula

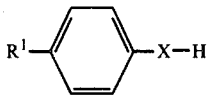

in which R¹ represents a chlorine atom or a tertiary butyl group and X an oxygen or sulfur atom with epihalogen hydrins, preferably epichlorhydrin, in the presence of bases, preferably alkali metal hydroxides, where the halogen hydrins of the general formula

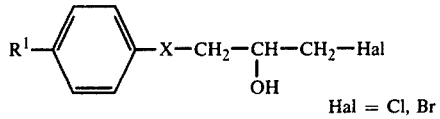

intermediately formed, where R¹ and X have the meaning given above, need not be isolated.

Halogen hydrins according to formula (10) in which R¹ stands for a chlorine atom or a tertiary butyl group and X represents an -NH-function are expediently isolated in pure form and converted into the unstable glycide ethers in the reaction mixture by addition of alkali metal hydroxides.

The following is a list of specific examples of carboxylic acids according to the invention, but the scope of the claim according to formula (1) is not to be limited thereby:

3-(4'-Carboxyphenoxy)-1-(4'-chlorphenoxy)-propanol-(2),
3-(3'Carboxyphenoxy)-1-(4'-chlorphenoxy)-propanol-(2),
3-[4'-(2-Carboxyvinyl)-phenoxy]-1-(4'-chlorphenoxy)-propanol-(2),
3-[3'-(2-Carboxyvinyl)-phenoxy]-1-(4'-chlorophenoxy)-propanol-(2),
3-[4'-(2-Carboxyäthyl)-phenoxy]-1-(4'-chlorphenoxy)-propanol-(2),
3-[3'(2-Carboxyäthyl)-phenoxy]-1-(4'-chlorphenoxy)-propanol-(2),
3-(4'-Carboxyphenoxy)-1-(4't-butylphenoxy)-propanol-(2),
3-(3'-Carboxyphenoxy)-1-(4'-t-butylphenoxy)-propanol-(2),
3-[4'-(2-Carboxyvinyl)-phenoxy]-1-(4'-t-butylphenoxy)-propanol-(2),
3-[3'-(2-Carboxyvinyl)-phenoxy]-1-(4'-t-butylphenoxy)-propanol-(2),
3-[4'-(2-Carboxyäthyl)-phenoxy]-1-(4'-t-butylphenoxy)-propanol-(2),
3-[3'-(2-Carboxyäthyl)phenoxy]-1-(4'-t-butylphenoxy)-propanol-(2),
3-(4'-Carboxyphenoxy)-1-(4'-chlorphenylamino)-propanol-(2),
3-(3'-Carboxyphenoxy)-1-(4'-chlorphenylamino)-propanol-(2),
3[4'-(2-Carboxyvinyl)-phenoxy-1-(4'-chlorphenylamino)-propanol-(2),
3-[3'-(2-Carboxyvinyl)-phenoxy]-1-(4'-chlorphenylamino)-propanol-(2),
3-[4'-(2-Carboxyäthyl)-phenoxy-1-(4'-chlorphenylamino)-propanol-(2),
3-[3'-(2-Carboxyäthyl)-phenoxy]-1-(4'-chlorphenylamino)-propanol-(2)
3-(4'-Carboxyphenoxy)-1-(4'-t-butylphenylamino)-propanol-(2),
3-(3'-Carboxyphenoxy)-1-(4'-t-butylphenylamino)-propanol-(2),
3-[4'-(2-Carboxyvinyl)-phenoxy]-1-(4'-t-butylphenylamino)-propanol-(2).
3-[3'-(2-Carboxyvinyl)-phenoxy]-1-(4'-t-butylphenylamino)-propanol-(2),
3[3'-(2-Carboxyvinyl)-phenoxy-1-(4'-t-butylphenylamino)-propanol-(2),
3-[4'-(2-Carboxyäthyl)-phenoxy]-1-(4'-t-butylphenylamino)-propanol-(2),
3-[3'-(2-Carboxyäthyl)-phenoxy]-1-(4'-t-butylphenylamino)-propanol-(2),
3-(4'-Carboxyphenylamino)-1-(4'-chlorphenoxy)-propanol-(2),
3-(3'-Carboxyphenylamino)-1-(4'chlorophenoxy)-propanol-(2),
3-[4'-(2-Carboxyvinyl)-phenylamino]-1-(4'-chlorphenoxy)-propanol-(2),
3-[3'(2-Carboxyvinyl)-phenylamino]-1-(4'chlorphenoxy)-propanol-(2),
3-[4'-(2-Carboxyäthyl)-phenylamino]-1-(4'chlorphenoxy)-propanol-(2),
3-[3'-(2-Carboxyäthyl)-phenylamino]-1-(4'chlorphenoxy)-propanol-(2),
3-(4'-Carboxyphenylamino)-1-(4'-t-butylphenoxy)-propanol-(2),
3(3'-Carboxyphenylamino)-1-(4'-t-butylphenoxy)-propanol-(2),
3-[4'-(2-Carboxyvinyl)-phenylamino]-1-(4'-t-butylphenoxy)-propanol-(2),
3-[3'-(2-Carboxyvinyl)-phenylamino]-1-(4'-t-butylphenoxy)-propanol-(2),
3-[4'-(2-Carboxyäthyl)p-phenylamino]-1-(4'-t-butylphenoxy)-propanol-(2),
3-[3'-(2-Carboxyäthyl)-phenylamino]-1-(4'-t-butylphenoxy)-propanol-(2),
3-(4'-Carboxyphenoxy)-1-(4'-chlorphenylmercapto)-propanol-(2),
3-(3'-Carboxyphenoxy)-1-(4'-chlorophenylmercapto)-propanol-(2),
3-[4'-(2-Carboxyvinyl)-phenoxy-1-(4'-chlorphenylmercapto)-propanol-(2),
3[3'-(2-Carboxyvinyl)-phenoxy]-1-(4'-chlorphenylmercapto)-propanol-(2),
3-[4'-(2-Carboxyäthyl)-phenoxy-1-(4'-chlorphenylmercapto)-propanol-(2),
3[3'(2-Carboxyäthyl)-phenoxy]-1-(4'-chlorphenylmercapto)-propanol-(2),
3-(4'-Carboxyphenoxy)-1-(4'-t-butylphenylmercapto)-propanol-(2),
3-(3'-Carboxyphenoxy)-1-(4'-t-butylphenylmercapto)-propanol-(2),
3-[4'-(2-Carboxyvinyl)-phenoxy]-1-(4't-butylphenylmercapto)-propanol-(2),
3-[3'(2-Carboxyvinyl)-phenoxy]-1-(4't-butylphenylmercapto)-propanol-(2),
3-[4'(2-Carboxyäthyl)-phenoxy]-1-(4't-butylphenylmercapto)-propanol-(2),
3-[3'-(2-Carboxyäthyl)-phenoxy]-1-(4'-t-butylphenylmercapto)-propanol-(2), their sodium, potassium, magnesium, aluminum, ammonium, triethanolammonium or diisopropylammonium salts, methyl, pyridyl-(3)-methyl, ethyl, 2-hydroxyethyl, 2-methyoxyethyl, 2-chloroethyl, 2-piperidyl-(1)-ethyl, 2-dimethylaminoethyl, allyl, n-propyl or isopropyl esters, also the nicotinic acid esters obtainable by esterifying the secondary hydroxyl group, the hydroxamates, and the aromatic acetals according to the invention.

The compounds of general formula (1) and their salts are preferably administered orally. Usually the oral daily dose for adults is 0.1 to 10 g, preferably 0.5 to 3 g.

The active substance may be made up for oral administration in conventional form, for example, in capsules, in liquid form, as tablets or as powders. By mixing with solid pulverulent vehicles, such as lactose, sucrose, sorbitol, mannitol, potato or maize starch, cellulose derivatives or gelatins, with or without addition of lubricants such as for example magnesium or calcium sterate, Carbowax ® or polyethylen glycols, they may be made up into tablets or dragee centers.

Other suitable dosage forms are rod capsules, for example of hard gelatin, or closed capsules of soft gelatin with a plasticizer, as for example glycerine. The rod capsules will preferably contain the active substance in granular form, for example mixed with fillers, such as lactose, sucrose, mannitol, starches such as for example potato starch, maize starch or amylopectin, cellulose derivatives, gelatins or highly disperse silicas. In soft capsules, the active substance is preferably dissolved or suspended in suitable liquids, for example vegetable oil or liquid polyethylene glycols.

In the following, the invention will be further illustrated by some practical examples.

EXAMPLE 1.
3-(4'-methoxycarbonylphenoxy)-1-(4'-chlorophenoxy)-propanol-(2)

To a solution of 1.12 g (0.02 mol) potassium hydroxide in 150 ml abs. methanol is added 18.30 g (0.12 mol) 4'-hydroxybenzoic acid methyl ester and the mixture slowly heated to boiling. In the course of 1 hour, 18.46 g (0.1 mol) 3-(4'-chlorophenoxy)-1,2-epoxypropane is added, and heated for 21 hours with reflux. Then the solvent is removed under vacuum, the residue is taken up in ether, and washed with water to neutral reaction. After drying the organic phase over sodium sulfate and concentrating under vacuum, there remains 25.05 g (74.4%) of crude product, which is recrystallized from carbon tetrachloride. Colorless crystals of m.p. 88°–90° C., yield 59.9%.

$C_{17}H_{17}ClO_5$ (336.78): Calc.: C,60.63; H, 5.09. Found: C, 60.59; H, 5.29.

IR-Spectrum (KBr)[1]: $\nu$(OH: 3500 cm$^{-1}$, $\nu$ (C=O): 1685 cm$^{-1}$.

(1) The IR spectrum were taken with a Perkin-Elmer instrument Type 257.
(2) The $^1$H NMR spectra were taken with a Varian spectrometer El 360, the chemical shifts are given in ppm relative to TMS ($\delta$=0.0), and the relative intensities are added in parentheses. s singlet, d doublet, t triplet, m multiplet.

$^1$H-NMR-Spectrum (CDCl$_3$)[2]: 2.7 d (1) OH, 3.8 n (3) COOCH$_3$, 4.2 m (4) CH$_2$, 4.3 m (1) CHOB. 6.7–8.1 m (8) Aromat.

EXAMPLE 2.
3-(4'-(2-methoxycarbonylvinyl)-phenoxy)-(4'-chlorophenoxy)-propanol-(2)

19.60 g (0.00 mols) 4'-hydroxycinnamic acid methyl ester and 18.46 (0.1 mol) 3-(4'-chlorophenoxy)-1, 2-epoxypropane are heated with a solution of 0.8 g (0.02 mol) sodium hydroxide in 150 ml absolute methanol for 18 hours with reflux. After removal of the solvent under vacuum, the residue is dissolved in chloroform and washed several times with dilute sodium hydroxide solution, then with water; the organic phase, dried over sodium sulfate and concentrated under vacuum, yields an oil that slowly solidifies. After recrystallization, there remain 28.5 g (78.5%) colorless crystals of m.p. 83°–84° C. (ethanol-water).

$C_{19}H_{19}ClO_5$ (562.82): Calc.: C, 62.90; H, 5.28. Found: C,63.26; H, 5.60.

IR-Spektrum (KBr): $\nu$ (OH): 3460 cm$^{-1}$, $\nu$ (C=O): 1715 cm$^{-1}$, $\nu$ (C=C): 1635 cm$^{-1}$.

$^1$HNMR-Spektrum (CDCl$_3$): 3.2 d (1) OH, 3.8 s (3) COOCH$_3$, 4.1 m (4) CH$_2$, 4.2 m (1) CHOH, 6.2 d (1) CH—CO, 7.6 d (1) CH—C$_6$H$_4$, 6.6–7.5 m (8) Aromat.

EXAMPLE 3.
3-(4'-(2-methoxycarbonyvinyl)-phenoxy)-1-(4'-chlorophenylmercapto)-propanol-(2)

In a solution of 0.56 g (0.01 mol) potassium hydroxide in 150 ml absolute methanol, 20.07 g (0.1 mol) 3-(4'-chlorophenylmercapto)-1,2-epoxypropane and 19.6 g (0.11 mol) 4'-hydroxycinnamic acid methyl ester are introduced at room temperature. After heating for 19 hours with reflux, the solvent is removed under vacuum, the residue taken up in chloroform, and extracted several times with dil. potassium hydroxide solution. After washing and drying over sodium sulfate, the organic phase is concentrated under vacuum, yielding 30.7 g (81.2%) crude product in the form of a yellow oil that gradually crystallizes.

M.p. 103° C. (benzene).

$C_{19}H_{19}ClO_4S$ (378.98): Calc.: C, 60.25; H, 5.05. Found: 59.87; H, 5.08.

Ir-Spectrum (KBr): $\nu$ (OH: 3150 cm$^-$, $\nu$ (C=O): 1700 cm$^{-1}$ $\nu$ (C=C): 1630 cm$^{-1}$.

$^1$H-NMR-Spectrum (d$_6$-Aceton): 3.3 d (2) SCH$_2$, 3.8 S (3) COOCH, 4.2 m (3) OCH$_2$CH, 4.6 d (1) OH, 6.3 d (1) CH—CO, 7.5 d (1) CH—C$_6$H$_4$, 6.8–7.6 m (8) Aromat.

EXAMPLE 4.
3-(4'-methoxycarbonylphenoxy)-1-(4'-chlorophenylamino)-propanol-2)

22.01 g (0.1 mol) 3-chloro-1-(4'chlorophenylamino)-propanol-(2), prepared by a known method (J. Am. Chem. Soc. 72, 3710, 1950), in 100 ml absolute methanol is treated with 6.17 g (0.11 mol) potassium hydroxide in 100 ml absolute methanol. Formation of the epoxide may be observed by the appearance of a precipitate. After adding 15.21 g (0.1 mol) 4'-hydroxybenzoic acid methyl ester, the reaction mixture is heated for 12 hours with reflux, the potassium chloride deposited is separated off, and the filtrate is concentrated under vacuum. The residue is digested several times with water and, after drying over phosphorus pentoxide (26.4 g, 78.6%), recrystallized for further purification. Colorless crystals of m.p. 126°–127° (ethylacetate).

$C_{17}H_{18}ClNO_4$ (335.79): Calc.: C, 60.91; H, 5.40; N, 417. Found: C, 60.35; H, 5.29; N, 4.26.

$C_{17}H_{18}ClNO_4$ (335.79): Ber.: C, 60.81; H, 5.40; N, 4.17. Cef.: C, 60.35; H, 5.29; N, 4.26

Ir-Specturm (KBr): $\nu$ (OH,NH): 3300 cm$^-$, $\nu$ (C=O): 1710 cm$^{-1}$, $^2$H-HMR-Spectrum (CDCl$_3$): 3.3 m (2) NCH$_2$, 3.8 s (3) COOCH$_3$, 3.9 – 4.6 m (5) NH, CHOH, OCH$_2$, 6.4 – 8.1 m (8) Aromat.

Example 5.
3-(4'-(2-methoxycarbonylvinyl)-phenoxy)-1-(4'-t-butylphenylamino)-propanol-(2)

Into a solution of 22.4 g (0.15 mol) 4'-tert.butylaniline in 100 ml methanol is introduced dropwise, at boiling heat, 23.42 g (0.1 mol) 3-(4'-(2-methoxycarbonylvinyl)-phenoxy)-1,2-epoxypropane in 100 ml methanol. This is followed by agitating for 45 minutes with reflux, concentrating under vacuum, and separating unreacted epoxide as well as excess amine present by fast distillation (138°/4 × 10$^{-2}$ mm). The oily residue crystallizes upon digesting with petroleum ether; colorless crystals of m.p. 114°-115° (ethylacetate/petroleum ether), yield 30.8 g (80.4%).

$C_{23}H_{29}HO_4$ (333.49): Calc.: C, 72.04; H, 7.62; N, 3.65. Found: C, 71.89; H, 7.58; N, 3.53.

IR-Spectrum (KBr): $\nu$(CH, NH): 3400 cm$^{-1}$ (Center of Absorption); $\nu$(C=O); 1710 cm$^{-1}$; $\nu$(C=C): 1630 cm$^{-1}$.

$^1$H-BNMR-Spectrum (CDCl$_3$): 1.3 s (9) C(CH$_3$)$_3$, 3.0 – 4.5 m (7) NHCH$_2$CH(OH)CH$_2$, 3.8 s (3) COOCH$_3$, 6.2 d (1) CH—CO, 7.5 d (1) CH—C$_6$H$_4$, 6.5 – 7.6 m (8) Aromat.

In a manner similar to the procedures described in Examples 1 to 5, other compounds of general formula (1) have beem prepared, and are listed in Table 1 below with physical characteristics. For the sake of completeness, the compounds already described in the examples have been included in the tables to follow.

EXAMPLE 6.
3-(4'-(2-methoxyethoxycarbonyl)-vinyl)-phenoxy)-1-(4'-chlorophenoxy)-propanol-(2)

While heating, 0.56 g (0.01 mol) potassium hydroxide is dissolved in 60 ml 2-methoxyethanol, and, after addition of 36.28 g (0.1 mol) 3-(4'-(2-methoxycarbonyl-vinyl)-phenoxy)-1-(4'-chlorophenoxy)-propanol-(2), heated with reflux for 5 hours. After addition of 200 ml water, the reaction mixture is extracted repeatedly with chloroform, and the combined organic phases are washed with water until neutral, dried over sodium sulfate and concentrated under vacuum. The oil remaining, upon treatment with acetic ester/petroleum ether, yields 21.5 g (52.8%) colorless crystals of m.p. 76°-77° C.

$C_{21}H_{23}ClO_6$ (406.8): Calc.: C, 62.00; H, 5.70. Found: C, 61.67; H, 5.48.

IR-Spectrum (KBr): $\nu$(OH): 3450 cm$^{-1}$, $\nu$(C=O): 1690 cm$^{-1}$, $\nu$(C=C): 1630 cm$^{-1}$.

$^1$H-NMR-Spectrum (CDCl$_3$): 3.4 s (3) OCH$_3$, 3.5 – 4.7 m (10) CH$_2$CH(OH)CH$_2$ CH$_2$CH$_2$, 6.2 d (1) CH—CO, 7.6 d (1) CH—C$_6$H$_4$, 6.6 – 7.6 m (8) Aromat.

Using the method illustrated in Example 6, other carboxylic acid esters according to formula (1) were prepared, as listed in Table 2.

Tab. 1

$$R^1-\underset{}{\underbrace{\bigcirc}}-X-CH_2-\underset{OH}{\underset{|}{CH}}-CH_2-Y-\underset{}{\underbrace{\bigcirc}}^{A-R^3} \quad (1)$$

| No. | R$^1$ | X | Y | A—R$^3$ | M.P. (° C)* | resp. B.P. (° C/mmHg)** |
|---|---|---|---|---|---|---|
| 1 | Cl | 0 | 0 | 4-COOCH$_3$ | 88–90 | (Carbon tetrachloride) |
| 2 | Cl | 0 | 0 | 4-COOCH$_2$CH$_3$ | 74 | (Ethanol/Water) |
| 3 | Cl | 0 | 0 | 4-COOCH$_2$CH=CH$_2$ | 49 | (Methylcyclohexane) |
| 4 | Cl | 0 | 0 | 4-COOCH$_2$CH$_2$CH$_3$ | 57 | (Ethylacetate/Petrolether) |
| 5 | Cl | 0 | 0 | 4-COOCH(CH$_3$)$_2$ | 72–3 | (Methylcyclohexane) |
| 6 | Cl | 0 | 0 | 3-COOCH$_3$ | 78–9 | (Cyclohexane) |
| 7 | Cl | 0 | 0 | 3-COOCH(CH$_3$)$_2$ | 192/6 × 10$^{-2}$ | |
| 8 | Cl | 0 | 0 | 4-CH=CH—COOCH$_3$ | 83–4 | (Ethanol/Water) |
| 9 | Cl | 0 | 0 | 4-CH$_2$CH$_2$COOCH$_3$ | 56–7 | ((Ethylacetate/Petrolether) |
| 10 | Cl | 0 | 0 | 4-CH=CHCOOCH$_2$CH$_3$ | 78–9 | (Petrolether) |
| 11 | Cl | 0 | 0 | 4-CH=CHCOOCH$_2$CH=CH$_2$ | 65–6 | (Diisopropylether) |
| 12 | Cl | 0 | 0 | 4-CH=CHCOOCH$_2$CH$_2$CH$_3$ | 61–2 | (Diisopropylether) |
| 13 | Cl | 0 | 0 | 4-CH=CHCOOCH(CH$_3$)$_2$ | 73–4 | (Diisopropylether) |
| 14 | Cl | 0 | 0 | 3-CH=CH—COOCH$_3$ | 77 | (Carbon tetrachloride) |
| 15 | Cl | 0 | 0 | 3-CH$_2$CH$_2$COOCH$_3$ | 200/8 × 10$^{-2}$ | |
| 16 | (CH$_3$)$_3$C | 0 | 0 | 4-COOCH$_3$ | 93–4 | (Methylcyclohexane) |
| 17 | (CH$_3$)$_3$C | 0 | 0 | 4-COOCH$_2$CH=CH$_2$ | 49–50 | (Diisopropylether) |
| 18 | (CH$_3$)$_3$C | 0 | 0 | 4-COOCH$_2$CH$_2$CH$_3$ | 72–3 | (Diisopropylether) |
| 19 | (CH$_3$)$_3$C | 0 | 0 | 4-COOCH(CH$_3$)$_2$ | 70–2 | (Diisopropylether) |
| 20 | (CH$_3$)$_3$C | 0 | 0 | 3-COOCH$_3$ | 73–4 | (Cyclohexane) |
| 21 | (CH$_3$)$_3$C | 0 | 0 | 4-CH=CHCOOCH$_3$ | 114 | (Ethylacetate) |
| 22 | (CH$_3$)$_3$C | 0 | 0 | 4-CH$_2$CH$_2$COOCH$_3$ | 232/1 × 10$^{-1}$ | |
| 23 | (CH$_3$)$_3$C | 0 | 0 | 4-CH=CHCOOCH$_2$CH$_2$CH$_3$ | 71–2 | (Ethylacetate/Petrolether) |
| 24 | (CH$_3$)$_3$C | 0 | 0 | 3-CH=CHCOOCH$_3$ | 56 | (Ethylacetate/Petrolether) |
| 25 | (CH$_3$)$_3$C | 0 | 0 | 3-CH$_2$CH$_2$COOCH$_3$ | 160/2 × 10$^{-2}$ | |
| 26 | Cl | NH | 0 | 4-COOCH$_3$ | 126–7 | (Ethylacetate) |
| 27 | Cl | NH | 0 | 3-COOCH$_3$ | 88–9 | (Ethylacetate/Petrolether) |
| 28 | Cl | NH | 0 | 4-COOCH(CH$_3$)$_2$ | 124 | (Ethylacetate) |
| 29 | Cl | NH | 0 | 4-CH=CHCOOCH$_3$ | 128 | (Petrolether) |
| 30 | Cl | 0 | NH | 4-COOCH$_3$ | 124–5 | (Methanol/Water) |
| 31 | Cl | 0 | NH | 4-COOCH$_2$CH$_3$ | 110 | (Petrolether) |
| 32 | Cl | 0 | NH | 3-COOCH$_2$CH$_3$ | 66–7 | (Ethylacetate/Petrolether) |
| 33 | (CH$_3$)$_3$C | 0 | NH | 4-COOCH$_3$ | 107–8 | (Ethylacetate/Petrolether) |
| 34 | (CH$_3$)$_3$C | 0 | NH | 3-COOCH$_2$CH$_3$ | 170/1 × 10$^{-2}$ | |
| 35 | (CH$_3$)$_3$C | NH | 0 | 4-COOCH$_3$ | 83–4 | (Ethylacetate/Petrolether) |
| 36 | (CH$_3$)$_3$C | NH | 0 | 3-COOCH$_3$ | 102 | (Ethylacetate/Petrolether) |
| 37 | (CH$_3$)$_3$C | NH | 0 | 4-CH=CH—COOCH$_3$ | 114–5 | (Ethylacetate/Petrolether) |
| 38 | Cl | S | 0 | 4-COOCH$_3$ | 67–8 | (Trichlorethylen/Petrolether) |
| 39 | Cl | S | 0 | 3-COOCH$_3$ | *** | |
| 40 | Cl | S | 0 | 4-CH=CH—COOCH$_3$ | 103 | (Benzol) |
| 41 | Cl | S | 0 | 4-CH$_2$CH$_2$—COOCH$_3$ | 60–1 | (Ethylacetate/Petrolether) |
| 42 | Cl | S | 0 | 3-CH=CHCOOCH$_3$ | 79–80 | (Ethylacetate/Petrolether) |
| 43 | (CH$_3$)$_3$C | S | 0 | 4-COOCH$_3$ | 190/8 − 5 × 10$^{-2}$ | |

*The melting points were determined with a Kofler melting point microscope and are uncorrected.
**Liquid products were purified with a laboratory fast distillation system (Leybold-Heraeus KDL 1); the boiling points given are jacket temperatures.
***Viscous oil purified by column chromatography.

Tab. 2

$$R^1-\phenyl-X-CH_2-CH(OH)-CH_2-Y-\phenyl-A-R^3$$

| No. | $R^1$ | X | Y | $A-R^3$ | M.P. (° C) | resp. B.P. (° C/mmHg) |
|---|---|---|---|---|---|---|
| 44 | Cl | O | O | 4-COOCH$_2$CH$_2$OH | 92 | (Benzol) |
| 45 | Cl | O | O | 4-COOCH$_2$CH$_2$OCH$_3$ | 71–2 | (Methylcyclohexane) |
| 46 | Cl | O | O | 4-CH=CHCOOCH$_2$CH$_2$OH | 97–8 | (Ethylacetate/Petrolether) |
| 47 | Cl | O | O | 4-CH=CHCOOCH$_2$CH$_2$OCH$_3$ | 76–77 | (Ethylacetate/Petrolether) |
| 48 | (CH$_3$)$_3$C | O | O | 4-COOCH$_2$CH$_2$OH | * | |
| 49 | (CH$_3$)$_3$C | O | O | 4-COOCH$_2$CH$_2$OCH$_3$ | 230/2×10$^{-3}$ | |
| 50 | (CH$_3$)$_3$C | O | O | 4-CH=CH—COOCH$_2$CH$_2$OH | 240/7×10$^{-2}$ | |
| 51 | (CH$_3$)$_3$C | O | O | 4-CH=CH—COOCH$_2$CH$_2$OCH$_3$ | 200/4×10$^{-2}$ | |
| 52 | Cl | NH | O | 4-COOCH$_2$CH$_2$OH | 124–5 | (Chloroform/Methanol) |

*Highly viscous oil, prufied by column chromatography.

EXAMPLE 7.

3-(4'-(2-carboxyvinyl)-phenoxy)-1-(4'-chlorophenoxy)-propanol-(2)

A suspension of 36.28 g (0.1 mol) 3-(4'-(2-methoxycarbonylvinyl)-phenoxy)-1-(4'-chlorophenoxy)-propanol-(2), 22.44 g (0.4 mol) potassium hydroxide, 60 ml ethanol and 30 ml water is heated for 4 hours with reflux, yielding a clear solution. The reaction mixture is then concentrated under vacuum, and the residue is dissolved in water and adjusted to pH 1 with 5N sulfuric acid. The precipitate is washed with water until neutral, dried over phosphorus pentoxide under vacuum and recrystallized for purification. Colorless crystals of m.p. 161°–162° C. (methanol), yield 31.33 g (89.7%).

$C_{18}H_{17}ClO_5$ (348.79): Calc.: C, 61.98; H, 4.91. Found: C, 61.82; H, 4.83.

IR-Spectrum (KBr): $\nu$(OH): 3600 cm$^{-1}$ und 3080-2500 cm$^{-1}$, $\nu$(C=O): 1680 cm$^{-1}$, $\nu$(C=C): 1630 cm$^{-1}$.

$^1$H-NMR-Spectrum (d$_6$-Aceton): 4.2 m (5) CH$_2$CHCH$_2$, 5.3 (Center of Absorption) s (2) OH, COOH, 6.3 d (1) CH—CO, 7.6 d (1) CH—C$_6$H$_4$, 6.8 – 7.7 m (8) Aromat.

Using the method illustrated in Example 7, other carboxylic acids according to formula (1) were prepared, as listed in Table 3.

Tab. 3

$$R^1-\phenyl-X-CH_2-CH(OH)-CH_2-Y-\phenyl-A-R^3 \quad (1)$$

| No. | $R^1$ | X | Y | $A-R^3$ | M.P. (° C) | |
|---|---|---|---|---|---|---|
| 53 | Cl | O | O | 4-COOH | 181 | (Ethylacetate) |
| 54 | Cl | O | O | 3-COOH | 174–5 | (Ethylacetate) |
| 55 | Cl | O | O | 4-CH=CH—COOH | 161–62 | (Methanol) |
| 56 | Cl | O | O | 4-CH$_2$CH$_2$COOH | 111–2 | (Ethylacetate/Petrolether) |
| 57 | Cl | O | O | 3-CH=CHCOOH | 153 | (Ethylacetate) |
| 58 | Cl | O | O | 3-CH$_2$CH$_2$COOH | 96 | (Ethylacetate/Petrolether) |
| 59 | (CH$_3$)$_3$C | O | O | 4-COOH | 154–5 | (Petrolether) |
| 60 | (CH$_3$)$_3$C | O | O | 3-COOH | 68–70 | (Carbon tetrachloride) |
| 61 | (CH$_3$)$_3$C | O | O | 4-CH=CHCOOH | 163 | (Ethylacetate) |
| 62 | CH$_3$)$_3$C | O | O | 4-CH$_2$CH$_2$COOH | 102–3 | (Ethylacetate/Petrolether) |
| 63 | (CH$_3$)$_3$C | O | O | 3-CH=CHCOOH | 138–40 | (Ethylacetate/Petrolether) |
| 64 | (CH$_3$)$_3$C | O | O | 3-CH$_2$CH$_2$COOH | 84–6 | (Benzol/Petrolether) |
| 65 | Cl | NH | O | 4-COOH | 168 | (Ethylacetate) |
| 66 | Cl | NH | O | 3-COOH | 151–2 | (Acetone/Water) |
| 67 | Cl | NH | O | 4-CH=CHCOOH | 184–6 | (Ethylacetate/Methanol) |
| 68 | Cl | O | NH | 4-COOH | 164 | (Methanol/Water) |
| 69 | Cl | O | NH | 3-COOH | 217–8 | (Methanol) |
| 70 | (CH$_3$)$_3$C | O | NH | 4-COOH | 150–2 | (Ethylacetate/Petrolether) |
| 71 | (CH$_3$)$_3$C | O | NH | 3-COOH | 130–1 | (Ethylacetate/Petrolether) |
| 72 | (CH$_3$)$_3$C | NH | O | 4-COOH | 188–9 | (Chloroform/Ethanol) |
| 73 | (CH$_3$)$_3$C | NH | O | 3-COOH | 155–6 | (Ethylacetate/Petrolether) |
| 74 | (CH$_3$)$_3$C | NH | O | 4-CH=CHCOOH | 171–2 | (Methanol) |
| 75 | Cl | S | O | 4-COOH | 111–2 | (Ethylacetate/Petrolether) |
| 76 | Cl | S | O | 3-COOH | 101–3 | (Acetone/Water) |
| 77 | Cl | S | O | 4-CH=CHCOOH | 146 | (Ethylacetate) |
| 78 | Cl | S | O | 4-CH$_2$CH$_2$COOH | 90–1 | (Ethylacetate/Petrolether) |
| 79 | Cl | S | O | 3-CH=CHCOOH | 129–31 | (Ethanol) |
| 80 | (CH$_3$)$_3$C | S | O | 4-COOH | 106–8 | (Ethylacetate/Petrolether) |
| 81 | (CH$_3$)$_3$C | S | O | 4-CH=CHCOOH | 132–5 | (Ethanol/Water) |

EXAMPLE 8.

3-(4'-pyridyl-(3)-methoxycarbonylphenoxy)-1-(4'-chlorophenoxy)-propanol-(2)

(a)

3-(4'-carboxyphenoxy)-1-(4'-chlorophenoxy)-propanol-(2) acetate.

A mixture of 32.28 g (0.1 mol) 3-(4'-carboxyphenoxy)-1-(4'-chlorophenoxy)-propanol-(2), 10.21 g (0.1 mol) acetic anhydride and 9.16 g (0.12 mol) anhydrous pyridine is agitated for 6 hours with reflux and then concentrated under vacuum. After recrystallizing the residue from isopropanol, 35.6 g (97.6%) colorless crystals, m.p. 159°–61° C., is obtained.

IR-Spectrum (KBr): $\nu$(OH): 3100-2540 cm$^{-1}$, $\nu$(C=O): 1735 cm$^{-1}$, $^1$H-NMR-Spectrum (CDCl$_3$): 2.1 s (3) CH₃CO, 4.2 m (4) CH₂, 5.4 m (1) CH—OCO, 6.7 - 8.1 m (9) Aromat, COOH.

(b)
3-(4'-chlorocarbonylphenoxy)-1-(4'-chlorophenoxy)-propanol-(2) acetate

A suspension of 36.48 g (0.1 mol) 3-(4'-carboxyphenoxy)-1-(4'-chlorophenoxy)-propanol-(2) acetate in 200 ml anhydrous chloroform is heated to boiling while agitating. The heat is then removed, and 17.85 g (0.15 mol) thionyl chloride is added so as to maintain reflux. After the exothermic reaction has subsided, heating to boiling is continued until evolution of gas ceases (approx. 4 hours), chloroform and excess thionyl chloride are removed under vacuum, and the residue is recrystallized from carbon tetrachloride. M.p. 81°-2° C., yield 37.0 g (96.5%).

IR-Spectrum (CHCl₃): $\nu$(C=O): 1770$^{-1}$, 1735 cm$^{-1}$.

¹H-NMR-Spectrum (CDCl₃): 2.1 s (3) CH₃CO, 4.3 m (4) CH₂, 5.4 m (1) CHOCO, 6.7 - 8.1 m (8) Aromat.

(c)

organic phase is dried over sodium sulfate and concentrated under vacuum.

To remove the protective group, the residue is dissolved in 70 ml methanol, treated with 20 ml conc, ammonia, and the mixture digested for several hours at room temprature. It is then concentrated under vacuum, and the residue is taken up in chloroform and washed with dilute sodium hydrogen carbonate solution as well as water. After drying over sodium sulfate, chloroform is removed under vacuum and the crude product is recrystallized. Colorless crystals, m.p. 107°-9° C. (methanol). Yield 11.7 g (28.3%).

C₂₂H₂₀ClNO₅ (413.87): Calc.: C, 63.85; H, 4.87; N, 3.38. Found: C, 63.74; H, 4.65; N, 3.29.

IR-Spectrum (KBr): $\nu$(OH): 3210 cm$^{-1}$, $\nu$(C=O): 1715 cm$^{-1}$.

¹H-NMR-Spectrum (d₆-Aceton): 4.2 m (5) CH₂CHCH₂, 4.7 s (1) OH, 5.3 s (2) COOCH₂, 6.8 - 8.8 m (12) Aromat.

Using the method illustrated in Example 8, other carboxylic acid esters according to formula (1) were prepared, as listed in Table 4.

Tab. 4

$$R^1-\bigcirc-X-CH_2-\underset{OH}{CH}-CH_2-Y-\bigcirc^{A-R^3} \quad (1)$$

| No. | R¹ | X | Y | A—R³ | M.P. (° C) resp. B.P. (° C/mmHg) |
|-----|-----|---|---|------|-----------------------------------|
| 82 | Cl | O | O | 4-COOCH₂CH₂Cl | 47-9 (Cyclohexane) |
| 83 | Cl | O | O | 4-COOCH₂CH₂N(CH₃)₂ | 72-3 (Methylcyclohexane) |
| 84 | Cl | O | O | 4-COOCH₂CH₂N⟨cyclohexyl⟩ | 99–101(Ethylacetate/ Petrolether) |
| 85 | Cl | O | O | 4-COOCH₂—⟨pyridyl⟩ | 107-9 (Methanol) |
| 86 | Cl | O | O | 4-CH=CHCOOCH₂CH₂Cl | |
| 87 | Cl | O | O | 4-CH=CHCOOCH₂CH₂N(CH₃)₂ | 104-6(Methylcyclohexane) |
| 88 | Cl | O | O | 4-CH=CHCOOCH₂CH₂N⟨cyclohexyl⟩ | 109-11 (Methylcyclohexane) |
| 89 | Cl | O | O | 4-CH=CHCOOCH₂—⟨pyridyl⟩ | 125-6 (Ethylacetate) |
| 90 | (CH₃)₃C | O | O | 4-COOCH₂CH₂Cl | |
| 91 | (CH₃)₃C | O | O | 4-COOCH₂CH₂N(CH₃)₂ | |
| 92 | (CH₃)₃C | O | O | 4-COOCH₂CH₂N⟨cyclohexyl⟩ | * |
| 93 | (CH₃)₃C | O | O | 4-COOCH₂—⟨pyridyl⟩ | |

* Viscous oil, purified by column chromatography.

3-(4'-pyridyl-(3)-methoxycarbonylphenoxy)-1-(4'-chlorophenoxy)-propanol-(2)

To a solution of 38.32 g (0.1 mol) 3-(4'-chlorocarbonylphenoxy)-1-(4'-chlorophenoxy)-propanol-(2) acetate in 50 ml absolute benzene, 13.21 g (0.12 mol) pyridyl-(3)-methanol is added dropwise and the mixture agitated for 5 hours with reflux. After addition of 50 ml benzene, it is extracted several times with water, and the

EXAMPLE 9.

3-(4'-(2-methoxycarbonylvinyl)-phenoxy)-1-(4'-chlorophenoxy)-propanol-(2-nicotinic acid ester 36.28 g (0.1 mol) 3-(4'-(2-methoxycarbonylvinyl)-phenoxy)-1-(4'-chlorophenoxy)-propanol-(2) and 17.80 g (0.1 mol) nicotinic acid chloride hydrochloride are treated with 100 ml absolute pyridine and agitated for 14 hours with reflux. After removal of precipitate, the pyridine is distilled off under vacuum, the residue is taken up ibn either, the ether phase is extracted repeatedly with water, dried over sodium sulfate and concentrated under vacuum. Further purification of the crude product is accomplished by column chromatography (silica gel 60 Merck, traveling medium benzene/ether 3/1); subsequent treatment of the product with petroleum either yields 18.15 g (39.0%) colorless crystals of m.p. 110°–112° C. (isopropanol).

$C_{25}H_{22}ClNO_6$ (467.92): Calc.: C, 64.17; H, 4.74; N, 2.99. Found: C, 63.69; H, 4.71; N, 3.19.

IR-Spectrum (CHCl$_3$): $\nu$(C=O): 1710 cm$^{-1}$ (Schwerpunkt), $\nu$(C=C): 1635 cm$^{-1}$.

$^1$H-NMR-Spectrum (CCl$_4$): 3.7 s (3) COOCH$_3$, 4.3 m (4) CH$_2$, 5.7 m (1), CHOCO, 6.2 d (1) CH—CO, 7.6 d (1) CH—C$_6$H$_4$, 6.6 – 9.2 m (12) Aromat.

Using the method illustrated in Example 9, other nicotinic acid esters according to formula (1) were similarly prepared, as listed in Table 5.

Tab. 5

| No. | R$^1$ | X | Y | A—R$^3$ | M.P. (° C) resp. B.P. (° C/mmHg) |
|---|---|---|---|---|---|
| 94 | Cl | 0 | 0 | 4-COOH | |
| 95 | Cl | 0 | 0 | 4-COOCH$_3$ | 200/1×10$^{-2}$ |
| 96 | Cl | 0 | 0 | 4-COOCH(CH$_3$)$_2$ | 137/7×10$^{-2}$ |
| 97 | Cl | 0 | 0 | 4-CH=CHCOOH | |
| 98 | Cl | 0 | 0 | 4-CH=CHCOOCH$_3$ | 110–12 (Isopropanol) |
| 99 | Cl | 0 | 0 | 4-CH$_2$CH$_2$COOCH$_3$ | 101–3 (Methanol/Water |
| 100 | Cl | 0 | 0 | 3-CH$_2$CH$_2$COOCH$_3$ | * |
| 101 | (CH$_3$)$_3$C | 0 | 0 | 4-COOH | |
| 102 | (CH$_3$)$_3$C | 0 | 0 | 4-COOCH$_3$ | 133–4 (Methanol) |
| 103 | (CH$_3$)$_3$C | 0 | 0 | 4-CH=CHCOOCH$_3$ | 106–8 (Methanol/Water |
| 104 | Cl | S | 0 | 4-COOCH$_3$ | * |

*HIghly visous oil, purified by column chromatography.

EXAMPLE 10.
3-(4'-(2-(n-hydroxycarbamoyl)-vinyl)-phenoxy)-1-(4'-chlorophenoxy)-propanol-(2)

13.9 g (0.2 mol) hydroxylamine hydrochloride and 13.33 g (0.3 mol) sodium hydroxide are dissolved in 200 ml aqueous ethanol (1:1). To this is added dropwise 36.28 g (0.1 mol) 3-(4'-(2-methoxycarbonylvinyl)-phenoxy)-1-(4'-chlorophenoxy)-propanol-(2) in 200 ml ethanol, and the mixture is agitated for 5 hours with reflux. After concentrating to dryness under vacuum, the residue is taken up in 250 ml water, the solution is acidified with dilute hydrochloric acid, and the precipitate is separated off and dried over phosphorus pentoxide. Colorless crystals of m.p. 108°–10° C. (acetone-water). Yield 28.4 g (78.2%).

$C_{18}H_{18}ClNO_5$(363.81): Calc.: C, 59.43; H, 4.98; Found: C, 59.36; H, 5.06.

IR-Spectrum (KBr): $\nu$(OH, NH): 3580–2700 cm$^{-1}$, $\nu$(C=O): 1655 cm$^{-1}$, $\nu$(C=C): 1625 cm$^{-1}$.

$^1$H-NMR-Spectrum (d$_6$-DMSO): 3,5 (Schwerpunkt) s (2) und 5.4 (Schwerpunkt) s (1) CHOH, NHOH, 4.1 m (5) CH$_2$CHCH$_2$, 6.3 d (1) CHCO, 7.5 d (1) CH—C$_6$H$_4$, 6.7 – 7.6 m (8) Aromat.

Using the method illustrated in Example 10, other carboxylic acid hydroxamates according to formula (1) were prepared, as listed in Table 6.

Tab. 6

| No. | R$^1$ | X | Y | A—R$^3$ | M.P. | (° C) |
|---|---|---|---|---|---|---|
| 105 | Cl | 0 | 0 | 4-CONHOH | 158–60 | (Methanol/Water) |
| 106 | Cl | 0 | 0 | 4-CH=CH—CONHOH | 108–10 | (Acetone/Water) |
| 107 | Cl | 0 | 0 | 4-CH$_2$CH$_2$CONHOH | 120–1 | (Ethylacetate) |
| 108 | (CH$_3$)$_3$C | 0 | 0 | 4-CONHOH | 133–55 | (Methanol/Water) |
| 109 | Cl | S | 0 | 4-CH$_2$CH$_2$CONHOH | 98–9 | (Ethylacetate/Petrolether) |

EXAMPLE 11.
3-(4'-(1,3-dioxolan-2-yl)-phenoxy)-1-(4'-chlorophenoxy)-propanol-(2)

A solution of 20.82 g (0.1 mol) 2-(4'-acetoxyphenyl)-1,3-dioxalane (prepared analogously to the method given in Bull. Soc. Chim. France 1972 (6), 2287) and 6.74 g (0.12 mol) potassium hydroxide in 100 ml isopropanol is treated in the course of 1 hour with 1.8 ml (0.1 mol) water and agitated for 3 hours at room temperature. Then 16.56 g (0.09 mol) 3-(4'-chlorophenoxy)-1,2-epoxypropane is added and the reaction mixture kept at 60° C. for another 6 hours. After concentrating the solvent under vacuum, the residue is taken up in ether, and the ethereal phase is extracted several times with 2% potassium carbonate solution, washed with water until neutral, and dried over sodium sulfate. The ether is removed under vacuum and the residue (20.9 g, 66.4%) distilled at 190° C. and 1 × 10$^{-1}$ mm. Colorless crystals, m.p. 58°–60° C. (petroleum ether).

$C_{18}H_{19}ClO_5$ (350.78): Calc.: C, C,61.63; H, 5.46. Found: C, 61.56; H, 5.48.

IR-Spectrum (KBr): $\nu$(OH): 3465 cm$^{-1}$, $\nu$(C—O—C—O—C): 1030–1170 cm$^{-1}$.

1H-NMR-Spectrum (CCl$_4$): 3.5 – 4.5 m (10) CH$_2$CH(OH)CH$_2$, CH$_2$CH$_2$, 5.6 s (1) CH—C$_6$H$_4$, 6.5 – 7.4 m (8) Aromat.

Using the method illustrated in Example 11, other acetals according to formula (1) were prepared, as listed in Table 7.

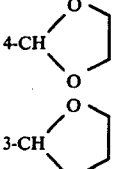

| No. | R$^1$ | X | Y | A—R$^3$ | M.P. (° C) resp. B.P. (° C/mmHg) |
|---|---|---|---|---|---|
| 110 | Cl | O | O | 4-CH(OCH$_2$CH$_3$)$_2$ | 175/4 × 10$^{-3}$ |
| 111 | Cl | O | O | 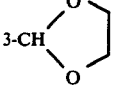 | 58–60 (Petrolether) |
| 112 | Cl | O | O | 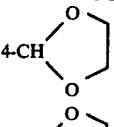 | 178/4 × 10$^{-3}$ |
| 113 | (CH$_3$)$_3$C | O | O | 4-CH(OCH$_3$)$_2$ | 185/3 × 10$^{-2}$ |
| 114 | (CH$_3$)$_3$C | O | O | 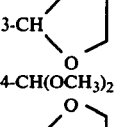 | 200/3 × 10$^{-3}$ |
| 115 | (CH$_3$)$_3$C | O | O | 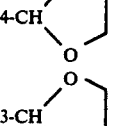 | 170/3 × 10$^{-3}$ |
| 116 | Cl | S | O | 4-CH(OCH$_3$)$_2$ | 165/4 × 10$^{-3}$ |
| 117 | Cl | S | O | 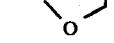 | 180/4 × 10$^{-3}$ |
| 118 | Cl | S | O | (3-CH dioxolane) | 175/3 × 10$^{-3}$ |

EXAMPLE 12. Medicinal drug containing 3-(4'-methoxycarbonylphenoxy)-1-(4'-chlorophenoxy)-propanol-(2)

100 g 3-(4'-methoxycarbonylphenoxy)-1-(4'-chlorophenoxy)-propanol-(2) is well mixed with 16 g maize starch and 6 g highly disperse silicon dioxide, then moistened with a solution of 2 g stearic acid, 6 g acetylcellulose and 6 g stearin in 70 ml isopropanol and granulated. The dried granulate is put through a sieve and, after mixing with 16 g maize starch, 16 g talc and 2 g magnesium stearate, molded into 1000 dragee centers. After coating with a sirup of 2 g lacca, 7.5 gum arabic, 0.15 g coloring, 2 g colloidal silicon dioxide, 25 g talc and 53.55 g sucrose, and drying, a thousand dragees each weighing 260 mg and containing 100 mg active substance are obtained.

EXAMPLE 13. Medicinal drug containing 3-(4'-carboxyphenoxy)-1-(4'-tert.-butylphenoxy)-propanol-(2)

250 g pulverized 3-(4'-carboxyphenoxy)-1-(4'-tert.-butylphenoxy)-propanol-(2) is mixed with 250 g lactose and 75 g starch, then treated with 16.5 g talc and 6.5 g calcium stearate, and, after mixing throughly, capsuled in one thousand hard gelatin capsules of suitable size, so that each capsule contains 250 mg active substance.

EXAMPLE 14. Medicinal drug containing 3-(4'-(2-methoxycarbonylethyl)-phenoxy)-1-(4'-tert.-butylphenoxy)-propanol-(2)

500 g 3-(4'-(2-methoxycarbonylethyl)-phenoxy)-1-(4'-tert.-butylphenoxy)-propanol-(2) is mixed with 500 g polyethylene glycol and packed in two thousand oval capsules of 500 mg capacity by the Scherer process.

EXAMPLE 15. Medicinal drug containing 3-(4'-methoxycarbonylphenoxy)-1-(4'-chlorophenoxy-propanol-(2) nicotinic acid ester 500 g 3-(4'-methoxycarbonylphenoxy)-1-(4'-chlorophenoxy)-propanol-(2) nicotinic acid ester is mixed with 500 g vegetable oil and packed in two thousand soft gelatin capsules (7.5) of 500 mg capacity by the Scherer process.

EXAMPLE 16. Pharmacological Testing

1. Oral tolerance

After oral administration of the test compounds to mice of strain NMR-I, weight 15–20 g, the acute toxicity was determined. LD$_{50}$ values were calculated following Litchfield-Wilcoxon (J. Pharmak, Exp. Therap. 96, 99, 1949) and pertain to the 8th day after treatment.

The LD$_{50}$ for clofibrate was 1900 mg/kg. The substances according to the invention were better tolerated and superior to clofibrate throughout.

2. Lipid-lowering action

Lipid-lowering action was tested on groups of 10 male Wistar rats (Ivanovas-Kisslegg), weight 200–220 g, normolipemic, on ordinary ration ("ssniff" complete feed).

The test compounds were taken up in an aqueous solution of 2.25% agar and 0.85% NaCl and administered orally. After administration of 4 × 100 mg/kg over a period of 3 days, the animals were bled by cardiac puncture after privation of food for 4 hours.[1]

[1] H. Enomoto and R. Zschocke, 3rd Int. Symp. Atheroscler, Berlin 1973, Abstr. 238.

Lipid lowering effect is expressed as percent lowering of total cholesterol and triglycerides compared to controls. Under the experimental conditions given above, clofibrate achieved an average lowering of total cholesterol by 37.4 ± 13.6% and of triglycerides by 50.4 ± 20.0% ($\bar{x} \pm S_x$ in each instance).[1] All compounds tested were superior to clofibrate in at least one score.

Table 8.

Percent lowering of triglycerides (TG) and total cholesterol (TC) levels in rat serum after oral administration of test substances.

| Compound Number | % Lowering TG $\bar{X} \pm S_x$ | % Lowering TC $\bar{X} \pm S_x$ |
|---|---|---|
| 1 | 63.8± 17.2 | 47.9 ± 10.2 |
| 2 | 60.2± 8.4 | 40.4± 24.3 |
| 3 | 68.6± 11.0 | 35.9± 18.1 |
| 4 | 74.2± 13.4 | 53.0± 7.5 |
| 5 | 54.6± 28.3 | 15.5± 14.7 |
| 6 | 78.1± 11.2 | 28.5± 10.0 |
| 7 | 73.2± 8.3 | 32.1± 18.1 |
| 8 | 52.1± 7.7 | 17.3± 26.0 |
| 9 | 87.9± 11.9 | 44.5± 17.5 |
| 10 | 77.4± 8.5 | 38.4± 5.6 |
| 11 | 40.2± 10.3 | 76.1± 3.7 |
| 12 | 67.0± 15.7 | 40.3± 10.8 |
| 13 | 79.7± 10.4 | 50.4± 7.3 |
| 14 | 64.8± 17.7 | 22.9± 5.2 |
| 17 | 83.4± 9.8 | 55.8± 7.1 |
| 18 | 68.3± 23.1 | 34.4± 6.9 |
| 19 | 72.9± 6.1 | 44.9± 8.0 |
| 22 | 79.0± 10.7 | 46.9± 11.4 |
| 23 | 77.9± 5.5 | 40.9± 9.3 |
| 26 | 81.0± 5.2 | 25.8± 23.7 |

Table 8.-continued

Percent lowering of triglycerides (TG) and total cholesterol (TC) levels in rat serum after oral administration of test substances.

| Compound Number | % Lowering TG $\overline{X} \pm S_x$ | TC $\overline{X} \pm S_x$ |
|---|---|---|
| 28 | 64.6± 16.9 | 30.8± 9.7 |
| 29 | 62.3± 10.7 | 12.7± 12.5 |
| 30 | 69.3± 15.9 | 12.1± 8.6 |
| 31 | 63.6± 18.5 | 33.3± 17.6 |
| 35 | 79.2± 9.0 | 51.9± 9.3 |
| 37 | 71.9± 13.5 | 32.8± 13.7 |
| 38 | 53.0± 17.6 | 12.3± 14.6 |
| 40 | 59.4± 14.7 | 9.6± 9.1 |
| 43 | 71.0± 12.5 | 37.2± 13.8 |
| 45 | 75.8± 17.1 | 51.7± 12.2 |
| 46 | 69.5± 8.9 | 32.3± 19.7 |
| 47 | 57.8± 10.7 | 44.4± 18.0 |
| 48 | 85.5± 15.6 | 60.4± 6.7 |
| 49 | 76.1± 14.6 | 33.1± 16.7 |
| 50 | 84.2± 5.4 | 49.3± 11.7 |
| 51 | 77.0± 7.4 | 47.8± 10.4 |
| 52 | 53.9± 13.3 | 50.0± 10.0 |
| 53 | 83.6± 15.5 | 40.5± 13.5 |
| 54 | 80.0± 11.4 | 28.7± 10.2 |
| 55 | 49.9± 23.7 | 45.4± 9.2 |
| 56 | 76.7± 7.7 | 48.0± 12.9 |
| 57 | 61.8± 10.9 | 28.4± 11.1 |
| 58 | 71.3± 7.6 | 42.2± 5.6 |
| 59 | 66.7± 8.1 | 45.7± 14.3 |
| 61 | 81.2± 17.1 | 44.9± 13.8 |
| 62 | 91.9± 5.0 | 38.7± 15.0 |
| 65 | 72.9± 11.3 | 20.9± 13.7 |
| 68 | 54.1± 17.0 | 15.2± 10.0 |
| 70 | 78.1± 10.4 | 33.3± 12.2 |
| 71 | 58.4± 15.5 | 28.9± 9.5 |
| 72 | 75.1± 9.9 | 53.7± 10.4 |
| 74 | 69.7± 9.6 | 50.7± 6.4 |
| 75 | 55.8± 14.2 | 32.2± 8.7 |
| 77 | 77.8± 12.0 | 55.5± 12.7 |
| 80 | 71.6± 18.6 | 48.2± 11.6 |
| 81 | 58.7± 14.8 | 27.5± 12.7 |
| 82 | 83.8± 6.0 | 53.9± 9.1 |
| 83 | 72.5± 11.1 | 46.2± 15.4 |
| 85 | 81.4± 5.9 | 52.0± 8.6 |
| 95 | 63.8± 14.8 | 38.3± 15.4 |
| 96 | 74.0± 4.8 | 36.8± 14.3 |
| 104 | 81.1± 5.6 | 48.0± 7.9 |
| 105 | 53.2± 11.2 | 29.8± 14.3 |
| 106 | 64.2± 17.1 | 43.9± 19.4 |
| 107 | 84.8± 4.1 | 49.6± 13.3 |
| 108 | 77.8± 3.3 | 51.1± 8.3 |
| 110 | 68.0± 6.5 | 32.1± 15.8 |
| 113 | 84.0± 8.8 | 44.4± 11.2 |
| 114 | 91.6± 4.8 | 67.9± 6.6 |
| 116 | 74.0± 9.8 | 43.2± 9.8 |

We claim:

1. A 1,3-disubstituted propanol-(2) derivative of the general formula:

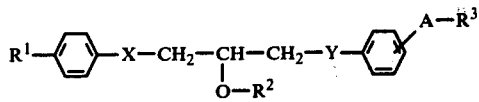

or its therapeutically acceptable salt, where X and Y stand for —O—;
$R^1 = $ —Cl, or —C(CH$_3$)$_3$;
$R^2 = $ —H;
A = a valence bond; and
$R^3 = $

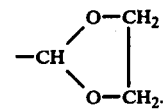

2. 3-(4'-(1,3-Dioxolan-(2)-yl)-phenoxy)-(4'-t-butylphenoxy)-propanol-(2).

3. A medicinal composition, for the treatment of hyperlipemia comprising an antihyperlipemically effective amount of a compound according to claim 1 as the active substance together with a pharmaceutically acceptable carrier.

4. Medicinal composition according to claim 3, characterized in that the single dose of the particular medicinal form contains 10–500 mg active substance.

5. A medicinal composition, for the treatment of hyperlipemia according to claim 4, wherein the active substance is 3-(4'-(1,3-dioxolan-(2)-yl)-phenoxy)-1-(4'-t.-butylphenoxy)-propanol-(2).

6. A method for treating hyperlipemia which comprises administering to a subject in need of such treatment, an antihyperlipemically effective amount of a compound according to claim 1.

7. A method for treating hyperlipemia which comprises administering to a subject in need of such treatment, an antihyperlipemically effective amount of a compound according to claim 2.

* * * * *

UNITED STATES PATENT AND TRADEMARK OFFICE
CERTIFICATE OF CORRECTION

PATENT NO. : 4,144,351

DATED : March 13, 1979

INVENTOR(S) : Grill et al.

It is certified that error appears in the above-identified patent and that said Letters Patent are hereby corrected as shown below:

Col. 3, line 20, "atoms" should read --atom--;
Col. 3, line 30, "corresponding" is misspelled;
Col. 3, line 49, "according the" should read --according to--;
Col. 5, line 34, "3-(3'Carboxyphenoxy)" should read --3-(3'-Carboxyphenoxy)--;
Col. 5, line 38, "(4'-chlorophenoxy)" should read --(4'-chlorphenoxy)--;
Col. 5, line 42, "3-[3'(2-" should read --3-[3'-(2- --;
Col. 5, line 44, "(4't-" should read --(4'-t- --;
Col. 5, line 55, "(2-Carboxyäthyl)phenoxy]" should read --(2-Carboxyäthyl)-phenoxy]--;
Col. 5, line 61, "3[4'" should read --3-[4'--;
Col. 5, line 65, "-phenoxy-" should read -- -phenoxy]- --;
Col. 6, delete lines 9 and 10 [which duplicate the preceding two lines];
Col. 6, line 17, "(4'chlorophenoxy)" should read --(4'-chlorphenoxy)--;

UNITED STATES PATENT AND TRADEMARK OFFICE
CERTIFICATE OF CORRECTION

PATENT NO. : 4,144,351  Page 2 of 5
DATED : March 13, 1979
INVENTOR(S) : Grill et al.

It is certified that error appears in the above-identified patent and that said Letters Patent are hereby corrected as shown below:

Col. 6, line 21, "3-[3'(2" should read --3-[3'-(2-- AND "1-(4'chlorphenoxy" should read --1-(4'-chlorphenoxy--;
Col. 6, line 23, "1-4'chlorphenox" should read --1-(4'-chlorphenox--;
Col. 6, line 25, "1-4'chlorphenox" should read --1-(4'-chlorphenox--;
Col. 6, line 29, "3(3'" should read --3-(3'--;
Col. 6, line 35, "(2-Carboxyäthyl)p-" should read --(2-Carboxyäthyl)- --;
Col. 6, line 41, "chlorophenylmercapto" should read --chlorphenylmercapto--;
Col. 6, line 43, "-phenoxy-" should read -- -phenoxy]- --;
Col. 6, line 45, "3[3'" should read --3-[3'--;
Col. 6, line 47, "-phenoxy-" should read -- -phenoxy]- --;
Col. 6, line 49, "3[3'(2" should read --3-[3'-(2--;
Col. 6, line 55, "1-(4't-" should read --1-(4'-t- --;
Col. 6, line 57, "3-[3'(2" should read --3-[3'-(2-- AND "1-(4't" should read --1-(4'-t--;
Col. 6, line 59, "3-[4'(2" should read --3-[4'-(2-- AND "1-(4't" should read --1-(4'-t--;
Col. 7, line 46, "C,60.59" should read --C,60.89--;
Col. 7, line 48, "(1) The IR spectrum" should read --(1) The IR spectra--;
Col. 7, lines 53-55, "$^1$H-NMR-Spectrum (CDCl$_3$)$^{(2)}$:2.7 d (1) OH, 3.8 n (3) COOCH$_3$, 4.2 m (4) CH$_2$, 4.3 m (1) CHOB. 6.7 - 8.1 m (8) Aromat" should read --$^1$H-NMR-Spectrum (CDCl$_3$)$^2$): 2.7 d (1) OH, 3.8 s (3) COOC$\underline{H}_3$, 4.2 m (4) C$\underline{H}_2$, 4.3 m (1) C$\underline{H}$OH, 6.7 - 8.1 m (8) Aromat.
Col. 7, footnotes (1) and (2) (lines 48-53), should appear after line 55 and before "EXAMPLE 2";

UNITED STATES PATENT AND TRADEMARK OFFICE
CERTIFICATE OF CORRECTION

PATENT NO. : 4,144,351  Page 3 of 5
DATED : March 13, 1979
INVENTOR(S) : Grill et al.

It is certified that error appears in the above-identified patent and that said Letters Patent are hereby corrected as shown below:

Col. 8, line 8, "$^1$HNMR" should read --$^1$H-NMR--;
Col. 8, lines 8-10, "3.2 d (1) OH, 3.8 s (3) COOCH$_3$, 4.1 m (4) CH$_2$, 4.2 m (1) CHOH, 6.2 d (1) CH-CO, 7.6 d (1) CH-C$_6$H$_4$, 6.6 - 7.5 m (8) Aromat" should read --3.2 d (1) OH, 3.8 s (3) COOCH$_3$, 4.1 m (4) CH$_2$, 4.2 m (1) CHOH, 6.2 d (1) CH-CO, 7.6 d (1) CH-C$_6$H$_4$, 6.6 - 7.5 m (8) Aromat--;
Col. 8, line 28, "(378.98)" should read --(378.88)--;
Col. 8, line 30, "3150 cm-," should read --3450 cm$^{-1}$,--;
Col. 8, line 33, "S (3) COOCH," should read --s (3) COOCH$_3$,--
Col. 8, lines 32-34, "3.3 d (2) SCH$_2$, 3.8 s (3) COOCH$_3$, 4.2 m (3) OCH$_2$CH, 4.6 d (1) OH, 6.3 d (1) CH-CO, 7.5 d (1) CH-C$_6$H$_4$, 618 - 7.6 m (8) Aromat" should read-3.3 d (2) SCH$_2$, 3.8 s (3) COOCH$_3$, 4.2 m (3) OCH$_2$CH, 4.6 d (1) OH, 6.3 d (1) CH-CO, 7.5 d (1) CH-C$_6$H$_4$, 6.8 - 7.6 m (8) Aromat.--;

Col. 8, line 39, "-2)" should read -- -(2)--;
Col. 8, line 54, "C,60.91" should read --C, 60.81--;
Col. 8, line 55, "417" should read --4.17--;
Col. 8, line 58, "Ir-Specturm (KBr): v(OH,NH):3300 cm-," should read --IR-Spectrum (KBr): v(OH,NH):3300 cm$^{-1}$,--;
Col. 8, line 60-61, all "H's" to be underlined;
Col. 8, line 60, "$^2$H-HMR" should read --$^1$H-NMR--;
Col. 9, line 10, "HO$_4$(333.49)" should read --NO$_4$(383.49)--;

Col. 9, line 12, "(CH, NH)" should read --(OH, NH)--;
Col. 9, line 15, "$^1$H-BNMR" should read --$^1$H-NMR--;
Col. 9, lines 15-17, all "H's" to be underlined;
Col. 9, line 21, "beem" should read --been--;

Col. 9, Tab. 1, No. 43, "5 x 10$^{-2}$" should read --15 x 10$^{-2}$--;
Col. 10, lines 21-23, all "H's" to be underlined;

UNITED STATES PATENT AND TRADEMARK OFFICE
CERTIFICATE OF CORRECTION

PATENT NO. : 4,144,351

DATED : March 13, 1979

INVENTOR(S) : Grill et al.

Page 4 of 5

It is certified that error appears in the above—identified patent and that said Letters Patent is hereby corrected as shown below:

Col. 11, footnote to Tab. 2, "prufied" should read --purified--;
Paragraph beginning Col. 11, line 67, All "H's" to be underlined;
Col. 12, line 68, after "$cm^{-1}$," --1675 $cm^{-1}$.-- should be inserted AND "$^{1}$H-NMR ..." should start a new line;
Col. 13, first two lines, All "H's" to be underlined;
Col. 14, line 4, "conc," should read --conc.--;
Col. 14, line 64, "(2-" should read --(2)--;
Col. 15, line 3, "ibn either" should read --in ether--;
Col. 15, line 9, "either" should read --ether--;
Col. 15, Tab. 5, footnote, "visous" should read --viscous--;
Col. 17, following line 6, insert the following heading: --Tab. 7--;

UNITED STATES PATENT AND TRADEMARK OFFICE
CERTIFICATE OF CORRECTION

PATENT NO. : 4,144,351  
DATED : March 13, 1979  
INVENTOR(S) : Grill et al.

Page 5 of 5

It is certified that error appears in the above—identified patent and that said Letters Patent is hereby corrected as shown below:

Col. 17, line 54, "7.5 gum" should read --7.5 g gum--;  
Col. 17, line 66, "throughly" should read --thoroughly--;  
Col. 18, line 11, "(4'-chlorophenoxy-" should read --(4'-chlorophenoxy)- --;  
Col. 18, line 35, "2.25%" should read --0.25%--;  
Col. 18, between lines 40 and 41, insert the following paragraph: --Serum lipids were determined with a Technicon autoanalyzer. Total cholesterol (TC) was tested by the Liebermann-Burchard reaction. Quantitative analysis for triglycerides (TG) was performed by Eggstein and Kreutz's enzyme method (Klin. Wschr. 44, 262, 1966), modified for autoanalyzer.--;  
Col. 20, line 22, "-(4'-t-butyl-" should read -- -1-(4'-t.-butyl- --.

Signed and Sealed this

Thirteenth Day of January 1981

[SEAL]

Attest:

SIDNEY A. DIAMOND

Attesting Officer

Commissioner of Patents and Trademarks